US00PP34490P2

(12) United States Plant Patent
Ullrich

(10) Patent No.: US PP34,490 P2
(45) Date of Patent: Aug. 16, 2022

(54) ROSE PLANT NAMED 'GEN R586'

(50) Latin Name: *Rosa hybrida*
Varietal Denomination: GEN R586

(71) Applicant: TECNOVIV LLC, Miami, FL (US)

(72) Inventor: Clarisse Ullrich, Quito (EC)

(73) Assignee: TECNOVIV LLC, Miami, FL (US)

( * ) Notice: Subject to any disclaimer, the term of this patent is extended or adjusted under 35 U.S.C. 154(b) by 0 days.

(21) Appl. No.: 17/669,120

(22) Filed: Feb. 10, 2022

(51) Int. Cl.
*A01H 5/02* (2018.01)
*A01H 6/74* (2018.01)

(52) U.S. Cl.
USPC ..... Plt./148

(58) Field of Classification Search
USPC ..... Plt./101, 141, 148
See application file for complete search history.

*Primary Examiner* — Karen M Redden
(74) *Attorney, Agent, or Firm* — C. Anne Whealy

(57) ABSTRACT

A new and distinct cultivar of Rose plant named 'GEN R586', characterized by its upright and strong flowering stems; vigorous growth habit; relatively large dark green-colored leaves; pink-colored flowers; and excellent postproduction longevity.

1 Drawing Sheet

Botanical designation: *Rosa hybrida.*
Cultivar denomination: 'GEN R586'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'GEN R586'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in February, 2016 of a proprietary Rose selection identified as Line R796, not patented, as the female, or seed, parent with a proprietary Rose selection identified as Line R771, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in April, 2017.

Asexual reproduction of the new Rose plant by bud grafting in El Quinche, Pichincha, Ecuador since June, 2017 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'GEN R586'. These characteristics in combination distinguish 'GEN R586' as a new and distinct Rose plant:

1. Upright and strong flowering stems.
2. Vigorous growth habit.
3. Relatively large dark green-colored leaves.
4. Pink-colored flowers.
5. Excellent postproduction longevity.

Plants of the new Rose differ from plants of the female parent selection in the following characteristics:

1. Plants of the new Rose are slightly shorter than plants of the female parent selection.
2. Flowers of plants of the new Rose have more petals than flowers of plants of the female parent selection.
3. Plants of the new Rose have pink-colored flowers whereas plants of the female parent selection have peach-colored flowers.

Plants of the new Rose differ from plants of the male parent selection in the following characteristics:

1. Plants of the new Rose are shorter than plants of the male parent selection.
2. Flowers of plants of the new Rose have more petals than flowers of plants of the male parent selection.
3. Plants of the new Rose have pink-colored flowers whereas plants of the male parent selection have cream-colored flowers.

Plants of the new Rose can also be compared to plants of *Rosa hybrida* 'Charming Unique', not patented. In side-by-side comparisons, plants of the new Rose differ from plants of 'Charming Unique' in the following characteristics:

1. Plants of the new Rose are more vigorous, taller and narrower than plants of 'Charming Unique'.
2. Plants of the new Rose have larger flowers with more petals per flower than plants of 'Charming Unique'.

BRIEF DESCRIPTION OF THE PHOTOGRAPH

The accompanying colored photographic sheet illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant. On the left side of the photographic sheet is a side perspective view of a typical flowering stein of 'GEN R586'. At the upper right of the photographic sheet is a close-up view of a typical developed flower of 'GEN R586'. And at the lower right of the photographic sheet are close-up views of the upper and lower surfaces of typical leaves of 'GEN R586'.

DETAILED BOTANICAL DESCRIPTION

The aforementioned photographs, following observations and measurements describe plants grown in ground beds in a polyethylene-covered greenhouse in Cayambe, Pichincha, Ecuador and under typical cut Rose production practices. Plants were pinched 14 weeks after planting and were 111 weeks old when the photograph and the description were taken. During the production of the plants, day temperatures ranged from 17° C. to 21° C., night temperatures ranged from 5° C. to 8° C. and light levels averaged 19,338 lux. In the following description, color references are made to The Royal Horticultural Society Colour Chart, 2015 Edition, except where general terms of ordinary dictionary significance are used.

Botanical classification: *Rosa hybrida* 'GEN R586'.

Parentage:

*Female, or seed, parent*.—Proprietary seedling selection of *Rosa hybrida* identified Line R796, not patented.

*Male, or pollen, parent*.—Proprietary seedling selection of *Rosa hybrida* identified Line R771, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Medium in thickness, fibrous; typically greyish brown in color, actual color of the roots is dependent on substrate composition, water quality, fertilizers, substrate temperature and age of roots.

*Rooting habit*.—Moderately freely branching; dense.

Plant description:

*Plant and growth habit*.—Perennial shrub; upright and strong flowering stems; typically grown as a standard type; vigorous growth habit and rapid growth rate.

*Productivity*.—Plants of the new Rose are highly productive with about 75.3 flowering stems developing per $m^2$ per year.

*Plant height*.—About 194 cm.

*Plant width* (*spread*).—About 71.8 cm.

*Lateral branches*.—Length: About 176.8 cm. Diameter: About 7.1 mm. Internode length: About 7.1 cm. Texture and luster: Smooth, glabrous; matte. Strength: Strong. Color, developing: Close to 146A and N199A. Color, developed: Close to 146A to 146B. Thorns: Density: About one to two thorns per linear cm. Height: About 7.1 mm. Length, at base: About 8.1 mm. Color, immature: Close to 185A. Color, mature: Close to 173A to 173C.

Leaf description:

*Arrangement*.—Alternate; compound with typically five leaflets per leaf.

*Leaf length*.—About 20.2 cm.

*Leaf width*.—About 14.4 cm.

*Leaflet length*.—About 7.5 cm.

*Leaflet width*.—About 4.5 cm.

*Leaflet shape*.—Ovate.

*Leaflet apex*.—Acuminate.

*Leaflet base*.—Obtuse.

*Leaflet margin*.—Serrate.

*Leaflet texture and luster, upper surface*.—Smooth, glabrous; semi-glossy.

*Leaflet texture and luster, lower surface*.—Smooth, glabrous; matte.

*Leaflet venation pattern*.—Pinnate.

*Leaflet color*.—Developing leaflets, upper surface: Close to 147A; at the margins, close to 184A. Developing leaflets, lower surface: Close to 184A. Fully expanded leaflets, upper surface: Close to 144A and 147A; venation, close to 144D. Fully expanded leaflets, lower surface: Close to 147C; venation, close to 144D.

*Petioles*.—Length: About 2.8 cm. Diameter: About 2 mm. Strength: Moderately strong. Texture and luster, upper surface: Smooth, glabrous; semi- glossy. Texture and luster, lower surface: Smooth, glabrous; matte. Color, upper surface: Close to 143C. Color, lower surface: Close to 143C and 145D.

*Stipules*.—Arrangement and appearance: Two, adnate to the petiole, leafy in appearance. Length: About 2.7 cm. Width: About 2.8 mm. Shape: Roughly deltoid. Apex: Acuminate, tapered. Base: Tapered. Margin: Variable. Texture and luster, upper and lower surfaces: Smooth, margins, pubescent; membranous; matte. Venation pattern: Pinnate.

Flower description:

*Flower type and arrangement*.—Symmetrical rosette flowers; flowers typically grown as standard types with one terminal flower per flowering stem; flowers face upright.

*Flowering season*.—Plants of the new Rose flower year-round under greenhouse conditions; early flowering habit, plants begin flowering about five weeks after pinching.

*Flower diameter*.—About 5.2 cm.

*Flower depth* (*height*).—About 5.8 cm.

*Flower longevity*.—Excellent postproduction longevity; flowers maintain good substance for about 61 days on the plant and for about eleven days as a cut flower; flowers persistent.

*Fragrance*.—Strongly fragrant; pleasant.

*Flower buds*.—Length: About 6.3 cm. Diameter: About 5.5 cm. Shape: Ovoid. Texture and luster: Smooth, glabrous; semi-glossy. Color: Close to 143B.

*Petals*.—Quantity: About 39 to 41 per flower; petals imbricate. Length: About 6.2 cm. Width: About 6.1 cm. Shape: Nearly orbicular. Apex: Blunt to short acute. Base: Obtuse. Margin: Entire; slightly undulate. Texture and luster, upper and lower surfaces: Smooth, glabrous; matte. Color: When opening, upper surface: Close to 37A; towards the base, close to 37D. When opening, lower surface: Close to 37A; towards the base, close to 37B and 2D. Fully opened, upper surface: Close to 38B; towards the base, close to 38D and 2D; venation, close to 150C; color becoming closer to 38A and N144A with subsequent development. Fully opened, lower surface: Close to 38B; towards the base, close to 38D and 2D; venation, close to 150B; color becoming closer to 38A and N144A with subsequent development.

*Petaloids*.—Quantity: About three to five in a single whorl; size and shape are variable. Texture and luster, upper surface: Somewhat rugose, glabrous; matte. Texture and luster, lower surface: Smooth, glabrous; matte. Color: When opening, upper and lower surfaces: Close to 39B to 39C. Fully opened, upper and lower surfaces: Close to 38A and 39D; venation, close to 38A and 39D; color becoming closer to 38B and N144A with subsequent development.

*Sepals*.—Quantity per flower: Typically five in a single whorl. Length: About 4.2 cm. Width: About 1.5 cm. Shape: Roughly deltoid. Apex: Tapered. Base: Truncate. Margin: Entire; ciliate. Texture and luster, upper and lower surfaces: Pubescent, leathery; matte. Color: When opening, upper and lower surfaces: Close to 143B. Fully opened, upper surface: Close to 143B. Fully opened, lower surface: Close to 143D.

*Reproductive organs*.—Stamens: Quantity: About 290 to 339 per flower. Filament length: About 1 cm. Filament color: Close to 1C. Anther size: About 2.9 mm by 1.5 mm. Anther shape: Reniform. Anther color: Close to 15A and 4C. Pollen amount: Scarce to moderate. Pollen color: Close to N25C. Pistils: Quantity: About 232 to 240 per flower. Pistil length: About 1 cm. Stigma diameter: About 0.9 mm. Stigma shape: Lobed. Stigma color: Close to 2A. Style length: About 9.5 mm. Style color: Close to 35C, 52B and 4D. Ovary color: Close to 157C. Receptacle height: About 1.5 cm. Receptacle diameter: About 1.4 cm. Receptacle shape: Cup-shaped. Receptacle texture: Smooth, glabrous. Receptacle color: Close to 143C. Fruits and seeds: To date, fruit and seed development have not been observed on plants of the new Rose.

Pathogen & pest tolerance: To date, plants of the new Rose have not been observed to be tolerant to pathogens and pests common to Rose plants.

Temperature tolerance: Plants of the new Rose have been observed to tolerate temperatures ranging from 9° C. to 23° C.

It is claimed:

1. A new and distinct Rose plant named 'GEN R586' as illustrated and described.

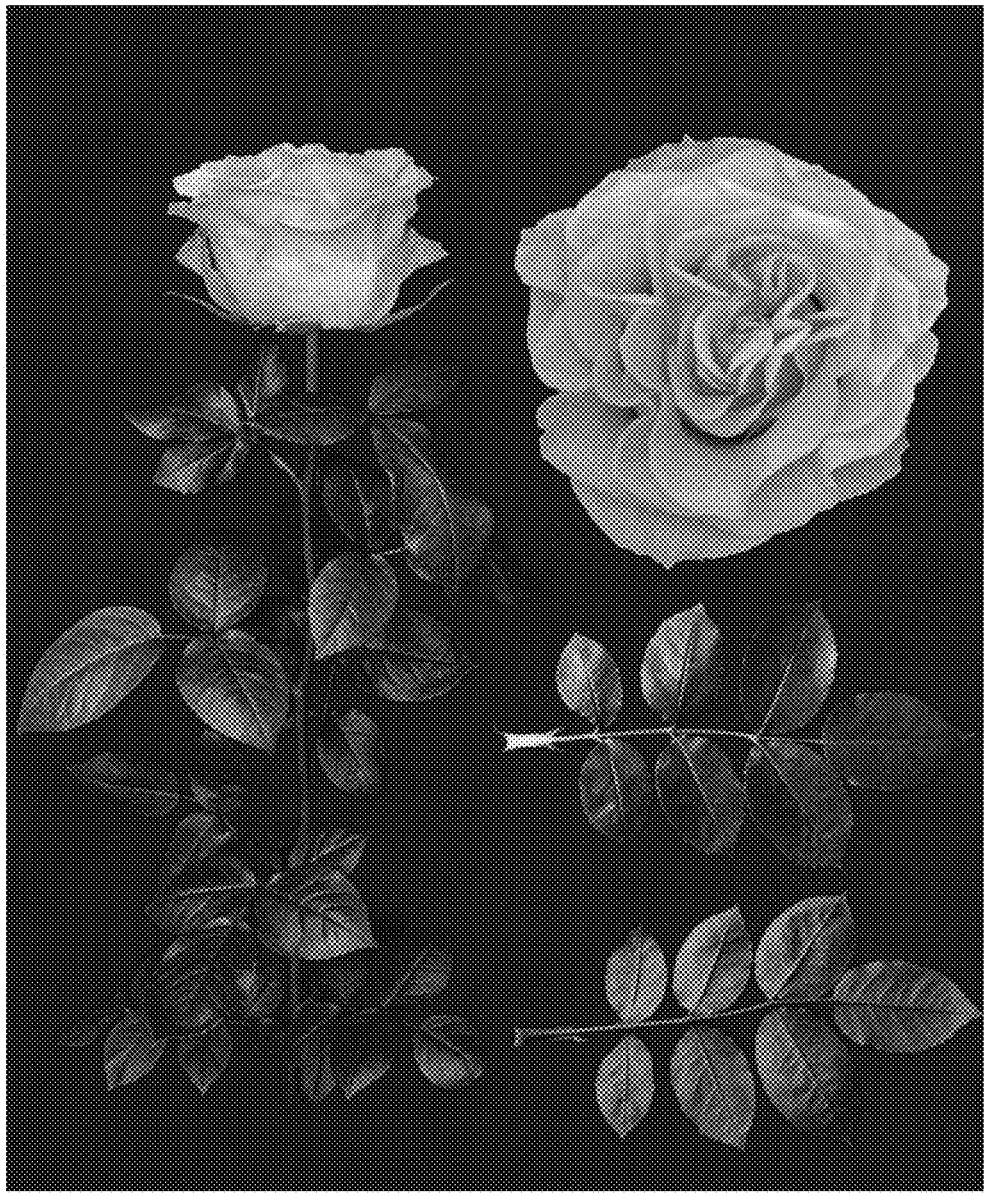

* * * * *